United States Patent [19]

Beech, Jr. et al.

[11] Patent Number: 5,382,743
[45] Date of Patent: Jan. 17, 1995

[54] SKELETAL ISOMERIZATION OF N-PENTENES USING ZSM-35 IN THE PRESENCE OF HYDROGEN

[75] Inventors: James H. Beech, Jr., Wilmington, Del.; Roland B. Saeger, Runnemede, N.J.; Robert A. Ware, Wyndmoor, Pa.

[73] Assignee: Mobil Oil Corporation, Fairfax, Va.

[21] Appl. No.: 51,930

[22] Filed: Apr. 26, 1993

[51] Int. Cl.⁶ .................. C07C 5/22; C07C 5/27
[52] U.S. Cl. .................. 585/671; 585/259; 585/260; 585/310; 585/324
[58] Field of Search ............... 585/671, 259, 260, 310, 585/324

[56] References Cited

U.S. PATENT DOCUMENTS

| | | | |
|---|---|---|---|
| 3,992,466 | 11/1976 | Plank et al. | 260/671 |
| 4,324,940 | 4/1982 | Dessau | 585/466 |
| 4,448,673 | 5/1984 | Shihabi | 585/739 |
| 4,503,282 | 3/1985 | Sikkenga | 585/329 |
| 4,886,925 | 12/1989 | Harandi | 585/331 |
| 4,922,048 | 5/1990 | Harandi | 585/310 |
| 4,996,386 | 2/1991 | Hamilton, Jr. et al. | 585/646 |
| 5,057,635 | 10/1991 | Gajda | 585/671 |
| 5,157,178 | 10/1992 | Gajda et al. | 585/666 |

FOREIGN PATENT DOCUMENTS

| | | |
|---|---|---|
| 0026041 | 4/1981 | European Pat. Off. |
| 0247802 | 12/1987 | European Pat. Off. |
| 0501577 | 9/1992 | European Pat. Off. |
| 0523838 | 1/1993 | European Pat. Off. |

*Primary Examiner*—Helen M. S. Sneed
*Assistant Examiner*—E. D. Irzinski
*Attorney, Agent, or Firm*—Alexander J. McKillop; Dennis P. Santini; Laurence P. Hobbes

[57] ABSTRACT

A method for conversion of linear C5 olefins in the presence of contaminant diolefins to corresponding iso-olefins of the same carbon number which comprises contacting a linear C5 olefin-containing organic feedstock with a catalyst comprising material having the structure of ZSM-35 under skeletal isomerization conditions, wherein said conversion is carried out at temperatures between about 100° and 750° C., weight hourly space velocities (WHSV) based on linear C5 olefins in said feedstock between 0.1 and 500 WHSV, C5 linear olefin partial pressures between 2 and 2000 kPa, and in the presence of hydrogen added in an amount sufficient to enhance linear C5 olefin conversion activity and extend the catalyst life of the catalyst relative to operation without any hydrogen added.

13 Claims, No Drawings

SKELETAL ISOMERIZATION OF N-PENTENES USING ZSM-35 IN THE PRESENCE OF HYDROGEN

FIELD OF THE INVENTION

This invention relates to a method for isomerizing linear pentenes to isopentenes (isoamylenes). The method further relates to the high level conversion of linear pentene-containing hydrocarbon feed streams to isopentene enriched product streams under skeletal isomerization conditions where the feed stream further comprises pentadiene impurities.

BACKGROUND OF THE INVENTION

The demand for iso-alkenes has recently increased. For example, relatively large amounts of isobutene are required for reaction with methanol or ethanol over an acidic catalyst to produce methyl tert-butyl ether (MTBE) or ethyl tert-butyl ether (ETBE) which is useful as an octane enhancer for unleaded gasolines. Isoamylenes are required for reaction with methanol over an acidic catalyst to produce tert-amyl methyl ether (TAME). With passage of the Clean Air Act in the United States mandating increased gasoline oxygenate content, MTBE, ETBE and TAME have taken on new value as clean-air additives, even for lower octane gasolines. Lead phasedown of gasolines in Western Europe has further increased the demand for such oxygenates.

An article by J. D. Chase, et al., *Oil and Gas Journal*, Apr. 9, 1979, discusses the advantages one can achieve by using such materials to enhance gasoline octane. The blending octane values of MTBE when added to a typical unleaded gasoline base fuel are RON=118, MON=101, R+M/2=109. The blending octane values of TAME when added to a typical unleaded gasoline base fuel are RON=112, MON=99, R+M/2=106.

The addition of shape-selective zeolite additives such as ZSM-5 to cracking catalysts, e.g., those used in fluidized catalytic cracking (FCC), is beneficial in producing gasoline boiling range product of increased octane rating. However, increased amounts of olefins result, including n-pentenes, creating a need for their conversion to higher value products such as isopentene which can be used to produce TAME.

Pentene exists in six isomers, three of which are linear, namely, 1-pentene, cis-2-pentene, and its stereo-isomer trans-2-pentene. Three isopentenes exist, 2-methyl-1-butene, 2-methyl-2-butene, and 3-methyl-1-butene, the latter not being active for TAME synthesis. Conversions between the 2-pentenes is known as geometric isomerization, whereas that between 1-pentene and the 2-pentenes is known as position isomerization, double-bond migration, or hydrogen-shift isomerization. The aforementioned three linear isomers are not branched and are known collectively as normal or n-pentenes. Conversion of the n-pentenes to the methyl-branched isopentenes is widely known as skeletal isomerization.

The reaction of tertiary olefins with alkanol to produce alkyl tertiary alkyl ether is selective with respect to iso-olefins. Linear olefins are unreactive in the acid catalyzed reaction, even to the extent that it is known that the process can be utilized as a method to separate linear and iso-olefins. The typical feedstream of FCC $C_5$ or $C_{5+}$ crackate used to produce tertiary alkyl ethers in the prior art which contains normal pentene and isopentene utilizes only the branched olefin in etherification. This situation presents an exigent challenge to workers in the field to discover a technically and economically practical means to utilize linear olefins, particularly normal butene, in the manufacture of tertiary alkyl ethers.

In recent years, a major development within the petroleum industry has been the discovery of the special catalytic capabilities of a family of zeolite catalysts based upon medium pore size shape selective metallosilicates. Discoveries have been made leading to a series of analogous processes drawn from the catalytic capability of zeolites in the restructuring of olefins.

European Patent Application 0026041 to Garwood, incorporated herein by reference, discloses a process for the restructuring of olefins in contact with zeolite catalysts having a constraint index of 1 to 12, e.g., ZSM-5 or ZSM-35, to produce iso-olefins in the presence of a diluent such as hydrogen or nitrogen, followed by the conversion of iso-olefins to MTBE and TAME. The restructuring conditions comprise temperatures between 204° C. and 315° C. and olefin pressures below 51 kPa.

In European Patent 0247802 to Barri et al., it is taught that linear olefins can be restructured in contact with zeolite catalyst, including Theta-1 (ZSM-22) and ZSM-23, to produce branched olefins. The restructuring conditions comprise temperature between 200°-550° C., pressure between 100 and 5000 kPa and WHSV between 1 and 100. Selectivities to isobutene up to 91.2% are reported using a calcined Theta-1 tectometallosilicate at 400° C. and 30.6% 1-butene conversion.

U.S. Pat. No. 3,992,466 to Plank et al. teaches the use of small crystal ZSM-35 as a catalyst for hydrocarbon conversion reactions, including "isomerization of aromatics, paraffins and olefins."

U.S. Pat. No. 4,324,940 to Dessau teaches the use of shape-selective zeolites having constraint index of 2 to 12, e.g., ZSM-35, for conducting selective skeletal isomerization of olefins wherein linear olefins are preferentially reacted when in mixed streams with non-linear olefins. Conversion conditions for isomerization include 450° to 1000° F., 0 to 500 psig, 0.1 to 200 WHSV, and hydrogen to olefin mole ratio of 0.1 to 100.

U.S. Pat. No. 4,922,048 to Harandi discloses the use of a wide variety of medium pore size zeolites, e.g., ZSM-5, ZSM-11, ZSM-12, ZSM-22, ZSM-23, ZSM-35 and ZSM-48, in low temperature (232°-385° C.) olefin interconversion of $C_2-C_6$ olefins to products including tertiary $C_4-C_5$ olefins and olefinic gasoline.

U.S. Pat. No. 4,886,925 to Harandi discloses low pressure high temperature conversion of light olefins to produce higher olefins rich in isoalkenes. The process converts $C_{2+}$ n-alkenes to a product comprising $C_4-C_6$ alkenes rich in iso-alkenes, $C_{7+}$ olefinic gasoline boiling range hydrocarbons, and unconverted hydrocarbons over ZSM-5. The reference teaches further treatment of the alkene effluent with methanol in the presence of medium pore size zeolites such as ZSM-5, ZSM-11, ZSM-12, ZSM-35, ZSM-38 and ZSM-48.

U.S. Pat. No. 4,996,386 to Hamilton, Jr. discloses concurrent isomerization and disproportionation of hydrocarbon olefins using a ferrierite/Mo/W/$Al_2O_3$ catalyst. The catalyst exemplified produces fewer branched olefins than a comparable material free of ferrierite and the reference teaches that ferrierite-containing catalysts exhibit improved selectivity to linear olefins than conventionally prepared disproportionation catalysts.

European Patent Application 0501577 to Grandvallet et al., Barri et al. teaches the conversion of a feedstock comprising linear olefins into a branched olefin rich product over ferrierite at an olefin partial pressure of more than 0.5 bar.

European Patent Application 0523838 to Powers et al., discloses a process to convert linear alkenes to methyl branched chain alkenes using one dimensional, medium pore zeolites such as H-ferrierite or ZSM-35.

Despite the efforts exemplified in the above references, the skeletal isomerization of olefins e.g., to produce isopentenes can be hampered by the presence of impurities in feeds which are used, such as C5+ FCC and linear olefin-containing recycle feeds from etherification. Such impurities can rapidly reduce the skeletal isomerization activity of the catalyst as well as its selectivity for isopentenes.

U.S. Pat. No. 4,544,792 to Smith et al. teach hydrogen co-feed inhibits coke formation on medium pore catalysts, e.g., HZSM-5, used to convert lower olefins and oxygenates to higher hydrocarbons.

U.S. Pat. No. 4,973,790 to Beech et al. teach hydrogen co-feed inhibits coke formation on medium pore catalysts, e.g., HZSM-5, used to oligomerize lower olefins to higher hydrocarbons in the presence of basic nitrogen compounds and dienes.

All of the above references are incorporated herein by reference.

SUMMARY OF THE INVENTION

The present invention provides a method for conversion of linear C5 olefins in the presence of contaminant C5 diolefins to corresponding iso-olefins of the same carbon number which comprises contacting a linear C5 olefin-containing organic feedstock with a catalyst comprising material having the structure of ZSM-35 under skeletal isomerization conditions, wherein said conversion is carried out at temperatures between about 100° and 750° C., weight hourly space velocities (WHSV) based on linear C5 olefins in said feedstock between 0.1 and 500 WHSV, C5 linear olefin partial pressures between 2 and 2000 kPa, and in the presence of hydrogen added in an amount sufficient to enhance linear C5 olefin conversion activity and extend the catalyst life of the catalyst relative to operation without any hydrogen added.

In an alternative embodiment the present invention provides a method for skeletal isomerization of a feedstock consisting essentially of C5 FCC product stream containing linear C5 olefins and C5 diolefins to a product enriched in C5 iso-olefins by contacting said feedstock with a catalyst comprising material having the structure of ZSM-35 and in the presence of added hydrogen, at a mole ratio of hydrogen to hydrocarbon of about 0.01:1 to about 10:1, and a mole ratio of hydrogen to diolefin of about 1:1 to about 1000:1.

The high selectivity of ZSM-35 in the present invention results in large part from isomerization occurring without significant conversion to lighter and heavier molecules. This phenomenon, it is believed, is a consequence of the pore structure of ZSM-35 which promotes isomerization at a much faster rate than the reaction by which say, butene, is converted to lighter (mostly propylene) and heavier olefins (olefin interconversion reaction). Moreover, such isomerization takes place without significant cracking of the feed or hydrogenation or dehydrogenation effects resulting in the formation of additional paraffins or diolefins.

DETAILED DESCRIPTION OF THE INVENTION

Feedstocks

Preferred feedstreams for use in the present invention include $C_5$ or $C_{5+}$ hydrocarbon feedstreams. Linear olefins suited to use in the present invention may be derived from a fresh feedstream comprising n-pentenes, or from the effluent of an iso-olefin etherification reactor which employs alkanol and $C_5$ or $C_{5+}$ hydrocarbon feedstock. Typical hydrocarbon feedstock materials for isomerization reactions according to the present invention include olefinic streams, such as cracking process gasoline boiling range product containing pentene isomers in mixture with substantial amounts of paraffins including n-pentanes and isopentanes. The $C_5$ components usually contain a major amount of unsaturated compounds, such as 15-40 wt % isopentenes, 10-30 wt % linear pentenes, and small amounts of linear and/or cyclic pentadienes, e.g., 0.05 to 2 wt %. Also, $C_{5+}$ heavier olefinic hydrocarbon streams may be used, e.g $C_5$ to $C_{10}$, preferably $C_5$ to $C_6$ olefinic hydrocarbon streams, e.g., FCC gasoline. The present invention is particularly suited to use with feedstreams containing relatively large diolefin concentrations, e.g., greater than 0.1 wt % total diolefins. Exemplary feedstreams can contain greater than 1 wt % pentadienes. Feedstocks comprising at least 5 wt % n-pentenes can be used in the present method.

In those embodiments wherein the present method has been incorporated in an integrated pentene isomerization/etherification process, e.g., TAME production, upstream hydrotreating can be used to remove pentadienes which can cause rapid deactivation of acidic etherification catalysts. In the event of an upstream hydrotreater tipset, hydrogen co-feed as employed by the present invention, allows reactivation of the isomerization catalyst without significant loss of stream time. In other applications of pentene skeletal isomerization, hydrogen co-feed can eliminate the need for upstream hydrotreating altogether.

Skeletal Isomerization Catalyst

The skeletal isomerization catalyst employed in the method of the present invention comprises a zeolite having the structure of ZSM-35, preferably having a crystal size whose largest dimension is no greater than 0.5 micron, preferably no greater than 0.25 micron, more preferably no greater than 0.15 micron, e.g., no greater than 0.1 micron.

ZSM-35 is more particularly described in U.S. Pat. No. 4,016,245, the entire contents of which are incorporated herein by reference.

For present purposes, "ZSM-35" is considered equivalent to its isotypes, which include ferrierite (P. A. Vaughan, Acta Cryst. 21, 983 (1966)); FU-9 (D. Seddon and T. V. Whittam, European Patent B-55,529, 1985); ISI-6 (N. Morimoto, K. Takatsu and M. Sugimoto, U.S. Pat. No. 4,578,259, 1986); monoclinic ferrierite (R. Gramlich-Meier, V. Gramlich and W. M. Meier, Am. Mineral. 70, 619 (1985)); NU-23 (T. V. Whittam, European Patent A-103,981, 1984); and Sr-D (R. M. Barter and D. J. Marshall, J. Chem. Soc. 1964, 2296 (1964)). Preferably the catalyst comprises ZSM-35 in its hydrogen-exchanged form, HZSM-35.

An example of a piperidine-derived ferrierite is more particularly described in U.S. Pat. No. 4,343,692, the entire contents of which are incorporated herein by reference. Other synthetic ferrierite preparations are described in U.S. Pat. Nos. 3,933,974; 3,966,883; 4,000,248; 4,017,590; and 4,251,499, the entire contents of all being incorporated herein by reference. Further descriptions of ferrierite are found in Bibby et al, "Composition and Catalytic Properties of Synthetic Ferrierite," Journal of Catalysis, 35, pages 256–272 (1974).

As noted above, microcrystalline ZSM-35 has a morphology whose largest dimension is no greater than 0.5 micron, preferably no greater than 0.25 micron or even 0.1. Even more preferably such crystals can be described as falling within the range of 0.03 to 0.08 micron by 0.03 to 0.08 micron by $\leq 0.05$ micron. Microcrystalline ZSM-35 is made by control of the synthesis formulation and synthesis temperature, with lower temperature favoring smaller crystals.

U.S. Pat. No. 3,992,466 to Plank et al., noted above, teaches the preparation of a small crystal ZSM-35 and its use as a catalyst for hydrocarbon conversion reactions.

The zeolite catalyst used is preferably at least partly in the hydrogen form, e.g., HZSM-35, but other cations, e.g., rare earth cations, may also be present. When the zeolites are prepared in the presence of organic cations, they may be quite inactive possibly because the intracrystalline free space is occupied by the organic cations from the forming solution. The zeolite may be activated by heating in an inert atmosphere to remove the organic cations e.g., by heating at over 500° C. for 1 hour or more. The hydrogen form can then be obtained by base exchange with ammonium salts followed by calcination e.g., at 500° C. in air. Other cations, e.g., metal cations, can be introduced by conventional base exchange or impregnation techniques.

The ZSM-35 may be incorporated in another material usually referred to as a matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic cracking reactions which are preferably minimized in the instant isomerization processes. Alternatively, silica-containing matrix containing a minor amount of aluminum may be employed. The relative proportions of finely divided ZSM-35 and inorganic oxide gel matrix vary widely with the zeolite content ranging from about 1 to about 90 percent by weight and more usually in the range of about 30 to about 80 percent by weight of the composite.

It is believed that using a silica binder and controlling extrusion conditions by means such as moisture control to ensure increased pore volume results in a catalyst which ages more slowly under skeletal isomerization conditions, resulting in increased cycle length. Such conditions increase total pore volume to greater than 0.6 g/cc, or 300+ angstroms pore volume to greater than 0.1 cc/g. These increased pore volumes can be obtained by increasing moisture content of the extrudate. The resulting catalyst composite is of particular utility insofar as its use can result in increased cycle length without any significant loss of iso-olefin selectivity.

In order to obtain desired linear olefin skeletal isomerization activity/selectivity, ZSM-35, preferably in the hydrogen form, should have an Alpha Value of at least 5, preferably at least 50 when used in the catalyst of the present invention. Alpha value, or alpha number, of a zeolite is a measure of zeolite acidic functionality and is more fully described together with details of its measurement in U.S. Pat. No. 4,016,218, *J. Catalysis*, 6, pp. 278–287 (1966) and *J. Catalysis*, 61, pp. 390–396 (1980). The experimental conditions cited in the latter reference are used for characterizing the catalysts described herein.

Process Conditions

In general terms, the method of the present invention can be conducted over a broad range of skeletal isomerization conditions including temperatures between about 100° and 750° C., weight hourly space velocities (WHSV) based on linear C5 olefins in said feedstock between 0.1 and 500 WHSV, and C5 linear olefin partial pressures between 2 and 2000 kPa. Hydrogen is added in an amount sufficient to enhance linear C5 olefin conversion activity and extend the catalyst life of the catalyst relative to operation without any hydrogen added.

Preferably, the skeletal isomerization is carried out at temperatures between about 150° and 600° C., weight hourly space velocities (WHSV) based on C5 linear olefins in said feedstock between 0.5 and 400 WHSV, linear olefin partial pressures between 10 and 500 kPa, C5 linear olefin conversion levels of at least 50 weight percent, a mole ratio of hydrogen to hydrocarbon of about 0.02:1 to about 10:1, a mole ratio of hydrogen to diolefin of about 2:1 to about 200:1, a hydrogen feed rate of 25 to 10000 scf $H_2$/bbl HC, and a hydrogen partial pressure of at least 75 kPa.

Even more preferably, the skeletal isomerization is carried out at temperatures of 315° to 425° C. in the presence of added hydrogen at a mole ratio of hydrogen to linear C5 olefin of 0.1:1 to 5:1, say, 0.1:1 to 3:1, or even 0.1:1 to 1:1, a mole ratio of hydrogen to C5 diolefin of 10:1 to 500:1, say, 10:1 to 300:1, or even 10:1 to 100:1, with the weight hourly space velocities (WHSV) based on linear C5 olefins in the feedstock being between 0.1 and 10 WHSV.

The examples which follow illustrate the invention without restricting it in any way.

EXAMPLE 1

Preparation of ZSM-35

1.18 parts of aluminum sulfate (17.2% $Al_2O_3$) were added to a solution containing 9.42 parts $H_2O$ and 1.38 parts of 50% NaOH solution in an autoclave. 0.03 parts of ZSM-35 seeds and 3.20 parts of Hi-Sil precipitated silica were added with agitation, followed by 1.0 part of pyrrolidine.

The reaction mixture had the following composition, in mole ratios:

| | |
|---|---|
| $SiO_2/Al_2O_3$ | 21.5 |
| $OH^-/SiO_2$ | 0.11 |
| $H_2O/Al_2O_3$ | 13.5 |
| $R/Al_2O_3$ | 6.45 |

EXAMPLE 2

Preparation of Silica-Bound HZSM-35

A catalyst was prepared by dry mixing the as-synthesized ZSM-35 of Example 1 with precipitated silica. Colloidal silica, in proportion to give 65% ZSM-35/35% silica after calcination, and water were added to the dry mix to obtain an extrudable mull. The mull was extruded to 1/16 inch (1.6 mm) diameter, dried at 120° C., calcined in nitrogen for three hours at 538° C., and then in air for 6 hours at 538° C. The extrudate was exchanged two times with 1N $NH_4NO_3$ solution at room temperature, rinsed with deionized water, dried at 120° C. and calcined in nitrogen for 3 hours at 538° C.

EXAMPLE 3

Isomerization of n-Pentenes with ZSM-35 at 370° C.

The above-prepared ZSM-35 prepared in accordance with Example 2 above was used in pentene skeletal isomerization reactions. The approximate experimental conditions were:

| | |
|---|---|
| Temperature | 370° C. |
| Pressure | 100 psia |
| n-pentene WHSV | 1.6 $hr^{-1}$ |
| $H_2$ feed rate | 360 scf/bbl of hydrocarbon feed |

The composition of the feed is set out in Table 1 below. Table 2 below provides n-pentene conversion and selectivities to tertiary $C_5$ olefins before and after hydrogen co-feed. Before 14 days on stream (DOS), nitrogen co-feed was used to maintain reactor pressure at 100 psia. In-situ reactivation was started by replacing nitrogen co-feed with hydrogen at the same partial pressure. Data at 12 and 13 DOS show rapid catalyst deactivation. The equivalent aging rate of these data is 38° F./day. Conversion of n-pentenes improved significantly when hydrogen co-feed was introduced, and selectivities to tertiary $C_5$ olefins (g iso-$C_5$= per g n$C_5$= converted) remained above 94%. The equivalent aging rate of the catalyst at 14 and 15 DOS during $H_2$ co-feed was 3° F./day.

TABLE 1

| Hydrocarbon Feed Composition (Wt %) | |
|---|---|
| $nC_5$ | 0.5 |
| $iC_5$ | 64.3 |
| $lC_5=$ | 33.4 |
| $iC_5=$ | 1.4 |
| $C_5==$ | 0.3 |

TABLE 2

| Skeletal Isomerization with Nitrogen and Hydrogen Co-Feed | | | | |
|---|---|---|---|---|
| | DOS (Days on Stream) | | | |
| | 12 | 13 | 14 | 15 |
| Temperature (°C.) | 370 | 370 | 370 | 370 |
| WHSV, g $nC_5=/h/g$ zeol. | 1.6 | 1.6 | 1.6 | 1.6 |
| Pressure, psia | 100 | 100 | 100 | 100 |
| $N_2$ partial P, psia | 24 | 24 | 0 | 0 |
| $H_2$ partial P, psia | 0 | 0 | 24 | 24 |
| Conversion, $nC_5=$ (wt %) | 46.5 | 24.6 | 72.2 | 70.2 |
| Selectivity, $iC_5=$ (wt %) | 99.9 | 99.9 | 94.5 | 95.4 |

What is claimed is:

1. A method for conversion of linear C5 olefins in the presence of contaminant diolefins to corresponding iso-olefins of the same carbon number which comprises contacting a linear C5 olefin-containing organic feedstock with a catalyst comprising material having the structure of ZSM-35 under skeletal isomerization conditions, wherein said conversion is carried out at temperatures between about 100° and 750° C., weight hourly space velocities (WHSV) based on linear C5 olefins in said feedstock between 0.1 and 500 WHSV, C5 linear olefin partial pressures between 2 and 2000 kPa, and in the presence of hydrogen added in an amount sufficient to enhance linear C5 olefin conversion activity and extend the catalyst life of the catalyst relative to operation without any hydrogen added.

2. The method of claim 1 wherein said conversion is carried out at temperatures of 315° to 425° C. in the presence of added hydrogen at a mole ratio of hydrogen to linear C5 olefin of 0.1:1 to 5:1, a mole ratio of hydrogen to C5 diolefin of 10:1 to 500:1, and said weight hourly space velocities (WHSV) based on linear C5 olefins in said feedstock are between 0.1 and 10 WHSV.

3. The method of claim 2 wherein said conversion is carried out in the presence of added hydrogen at a mole ratio of hydrogen to linear C5 olefin of 0.1:1 to 3:1, and a mole ratio of hydrogen to C5 diolefin of 10:1 to 300:1.

4. The method of claim 2 wherein said conversion is carried out in the presence of added hydrogen at a mole ratio of hydrogen to linear C5 olefin of 0.1:1 to 1:1, and a mole ratio of hydrogen to C5 diolefin of 10:1 to 100:1.

5. The method of claim 1 wherein said organic feedstock contains at least 0.005 wt % diolefins.

6. The method of claim 2 wherein said organic feedstock contains at least 0.01 wt % pentadiene.

7. The method of claim 1 wherein said organic feedstock comprises C5 FCC product.

8. The method of claim 1 wherein said organic feedstock comprises C5 effluent from a TAME etherification process.

9. The method of claim 1 wherein said catalyst comprises an inorganic oxide binder.

10. The method of claim 1 wherein said catalyst comprises a silica binder.

11. A method for skeletal isomerization of a feedstock consisting essentially of C5 FCC product stream containing linear C5 olefins and C5 diolefins to a product enriched in C5 iso-olefins, at C5 linear olefin conversion levels of at least 50 weight percent, by contacting said feedstock with a catalyst comprising material having the structure of ZSM-35 and in the presence of added hydrogen, at a mole ratio of hydrogen to hydrocarbon of about 0.01:1 to about 1:1, and a mole ratio of hydrogen to diolefin of about 2:1 to about 200:1.

12. The method of claim 11 wherein said contacting is carried out at temperatures between about 150° and 600° C., weight hourly space velocities (WHSV) based on C5 linear olefins in said feedstock between 0.5 and 400 WHSV, linear olefin partial pressures between 10 and 500 kPa, a mole ratio of hydrogen to hydrocarbon of about 0.02:1 to about 10:1, a mole ratio of hydrogen to diolefin of about 2:1 to about 200:1, a hydrogen feed rate of 25 to 10000 scf $H_2$/bbl hydrocarbon and a hydrogen partial pressure of at least 75 kPa.

13. The method of claim 11 wherein said contacting is carried out at temperatures between about 100° and 750° C., weight hourly space velocities (WHSV) based on linear olefins in said feedstock between 0.1 and 500 WHSV, and linear olefin partial pressures between 2 and 2000 kPa.

* * * * *

Adverse Decisions in Interference

Patent No. 5,382,743, James H. Beech, Jr., Roland B. Saeger, Robert A. Ware, SKELETAL ISOMERIZATION OF N-PENTENES USING ZSM-35 IN THE PRESENCE OF HYDROGEN, Interference No. 103,902, final judgment adverse to the patentees rendered March 4, 1999, as to claims 1-13.
*(Official Gazette May 25, 1999)*

Adverse Decisions in Interference

Patent No. 5,382,743, James H. Beech, Jr., Roland B. Saeger, Robert A. Ware, SKELETAL ISOMERIZATION OF N-PENTENES USING ZSM-35 IN THE PRESENCE OF HYDROGEN, Interference No. 103,902, final judgment adverse to the patentees rendered March 4, 1999, as to claims 1-13.
*(Official Gazette June 8, 1999)*